United States Patent [19]

Pier

[11] Patent Number: 4,578,458

[45] Date of Patent: Mar. 25, 1986

[54] MUCOID EXOPOLYSACCHARIDE VACCINE AGAINST *PSEUDOMONAS AERUGINOSA*

[75] Inventor: Gerald B. Pier, Brookline, Mass.

[73] Assignee: Brigham and Women's Hospital, Boston, Mass.

[21] Appl. No.: 477,958

[22] Filed: Mar. 23, 1983

[51] Int. Cl.$^4$ .................... C08B 37/00; A61K 39/104; C12P 19/04
[52] U.S. Cl. .................................... 536/123; 424/88; 424/92; 435/101; 435/253; 536/1.1
[58] Field of Search ....................... 531/1; 424/88, 92; 536/1, 123; 435/101

[56] References Cited

U.S. PATENT DOCUMENTS 4,285,936  8/1981  Pier et al. .............................. 424/92

OTHER PUBLICATIONS

Chemical Abstracts, vol. 98, Abst. No. 213950v, 1983.

*Primary Examiner*—Blondel Hazel
*Attorney, Agent, or Firm*—Oblon, Fisher, Spivak, McClelland & Maier

[57] ABSTRACT

A method of inducing an immune response against multiple strains of *Pseudomonas aeruginosa* which comprises administering to a human or animal an amount of mucoid exopolysaccharide from *Pseudomonas aeruginosa* 2192 sufficient to induce an immune response in the human or animal is disclosed along with the microorganism which produces this antigen and a method of separating the antigen from the crude bacterial slime.

3 Claims, 1 Drawing Figure

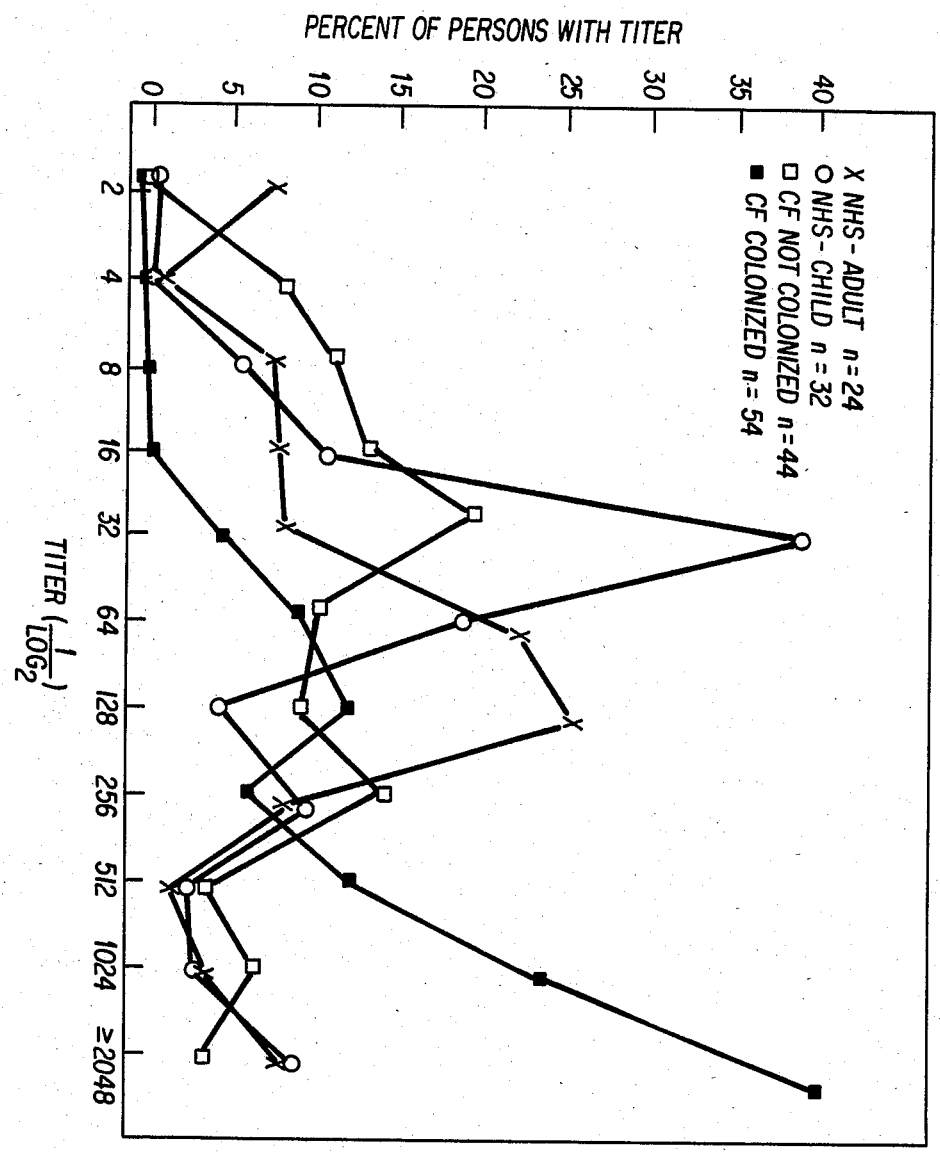

MUCOID EXOPOLYSACCHARIDE VACCINE AGAINST *PSEUDOMONAS AERUGINOSA*

The investigations leading to the present invention were supported in part by grant number AI 15835 from the NIAID division of the National Institutes of Health and by contract number DAMD-17-79-C-9050 from the U.S. Army Medical Research and Development Command.

BACKGROUND OF THE INVENTION

1. Field of the Invention

The present invention relates to a mucoid exopolysaccharide isolated from a particular strain of *Pseudomonas aeruginosa*, to a method of using this compound, and to a general method capable of isolating this compound.

2. Description of the Prior Art

*Pseudomonas aeruginosa* infection is a particularly important problem for patients with cystic fibrosis since more than 70% of patients with cystic fibrosis harbor *P. aeruginosa* in their lungs. Up to 90% of cystic fibrosis patients who survive to adulthood will have had chronic obstructive bronchitis associated with *P. aeruginosa* at some time during their lives.

Most of the strains of pseudomonas bacteria isolated from patients with cystic fibrosis produce a peculiar polysaccharide slime-like material that has been characterized as a polymer of uronic acids. These so-called "mucoid" pseudomonas strains are considered virtually pathognomonic of cystic fibrosis when isolated from a patient with bronchitis. Production of this slime coating is observed among only one to two percent of pathogenic pseudomonas isolates from other sources. The slime coating, which makes removal of the bacterial colonies difficult, is believed to contribute to the persistence of these slime-generating pseudomonas strains in the lungs of patients with cystic fibrosis.

Various polysaccharides have previously been used to induce immune responses in animals. These include certain mucoid exopolysaccharide from pseudomonas strains (Macone, Pier, et al, *N. Engl. J. Med.*, 304, 1445-1449 (1981)). However, all of the previous mucoid exopolysaccharide isolates were not of general use as a vaccine against all strains of *Pseudomonas aeruginosa* because of strain specificity of the immunogenic response. Accordingly, a mucoid exopolysaccharide vaccine capable of inducing a vigorous immune response against multiple strains of *Pseudomonas aeruginosa* is still needed.

SUMMARY OF THE INVENTION

It is an object of the present invention to provide a vaccine capable of inducing an immune response against multiple strains of *Pseudomonas aeruginosa*.

It is a further object of this invention to provide a method of isolating such a vaccine from *Pseudomonas aeruginosa*.

It is yet another object of this invention to provide a method of inducing an immune response against *Pseudomonas aeruginosa* strains which produce mucoid exopolysaccharide.

These and other objects of the invention as will hereinafter become more readily apparent have been accomplished by providing a bacterial antigen comprising mucoid exopolysaccharide having the antigenic characteristics of *Pseudomonas aeruginosa* strain 2192. Other objects of the invention have been accomplished by providing a method of purifying mucoid polysaccharide from bacteria, which comprises the steps of precipitating mucoid polysaccharide from an aqueous solution of said polysaccharide by adding a divalent cation, whereby a precipitate and a supernatant are formed; separating said supernatant from said precipitate; dissolving said precipitate in an aqueous solution containing a divalent cation chelating agent, whereby a solution containing purified mucoid polysaccharide and a residue are obtained; and separating said solution containing purified mucoid polysaccharide from said residue. Other objects of the invention have been accomplished by providing a method of inducing an immune response against multiple strains of *Pseudomonas aeruginosa*, which comprises administering to a human or animal an amount of mucoid exopolysaccharide from *Pseudomonas aeruginosa* strain 2192 sufficient to induce an immune response in said human or animal. Other objects of the invention have been accomplished by providing *Pseudomonas aeruginosa* strain 2192 in biologically pure form.

BRIEF DESCRIPTION OF THE DRAWING

A more complete appreciation of the invention and many of the attendant advantages thereof will be readily obtained as the invention becomes better understood by reference to the following detailed description when considered in connection with the accompanying drawing wherein:

The FIGURE shows a frequency distribution plot of antibody titers determined in a hemagglutination assay found in sera obtained from normal adults (NHS-A), normal children (NHS-C), and cystic fibrosis (CF) patients, either culture-positive or culture-negative for mucoid exopolysaccharide in spatum.

DESCRIPTION OF THE PREFERRED EMBODIMENTS

Microorganisms suitable for use in carrying out the invention described herein are exemplified by cultures now on deposit with the American Type Culture Collection, 12301 Parklawn Drive, Rockville, Md. 20852, U.S.A. These cultures were deposited on Mar. 23, 1983 and are identified by ATCC No. 39324. Prior to this deposit, *Pseudomonas aeruginosa* strain 2192 was not available outside the laboratory of the inventor.

The present invention has resulted from the discovery that a particular strain of bacteria, *Pseudomonas aeruginosa* 2192, produces a mucoid exopolysaccharide having a common immunological determinant capable of inducing a strong immune response against multiple strains of *Pseudomonas aeruginosa*. By "having the antigenic characteristics of" is meant that two molecules elicit substantially the same overall immune response. In the present case, the mucoid exopolysaccharide from *P. aeruginosa* is believed to consist essentially of a single determinant, although a minor amount of one or more other determinants may be present at levels that are presently undetected. While some of the *P. aeruginosa* organisms previously known may have exhibited the same determinant, no *P. aeruginosa* organism is known to have expressed a mucoid exopolysaccharide consisting essentially of this determinant. Accordingly, such mucoid exopolysaccharides having multiple determinants are not encompassed by the present invention since if they elicit an immune response, it will be a mixed immune response against all of the determinants present in the molecules, i.e., they will not have the entire "antigenic characteristics" of *P. aeruginosa* 2192. Furthermore, new strains of *P. aeruginosa* may be discovered or created in the future which produce a polysaccharide which consist essentially of the same determinants present in *P. aeruginosa* 2192. Such mucoid exopolysaccharides would have the same antigenic characteristics as *P. aeruginosa* 2192 and thus would be encompassed by the present invention.

By mucoid exopolysaccharide is meant an external polysaccharide comprising a polymer of uronic acids, especially one consisting principally of mannuronic and guluronic acids. The antigenic determinant of strain 2192 mucoid exopolysaccharide resides in the chemical arrangement of the uronic acid groups. Only one principal determinant, which also appears broadly in other strains, appears to be present in strain 2192. Previous investigators had shown that mucoid exopolysaccharides from other strains of *Pseudomonas aeruginosa* produced antibodies specific for those strains. These investigators had either reported the absence of a response to mucoid exopolysaccharide or had indicated that serotype specific determinants obscured the expression of any common determinant or multiple strains of this bacteria. See, for example, Hoiby et al, *Acta Pathol. Microbiol. Scand.* [C], 83: 459–468 (1975) and Lam et al, *Infect. Immun.*, 28: 546–556 (1980). Thus, the present invention represents a significant advance in producing a vaccine against multiple strains of *Pseudomonas aeruginosa*.

*Pseudomonas aeruginosa* 2192 was obtained from a cystic fibrosis patient. *P. aeruginosa* 2192 may be maintained and subcultured in any liquid basal medium containing nutrients sufficient to allow the growth of this organism. Typically, the medium is buffered and contains known essential ingredients for growth, such as a nitrogen source, carbon source, co-factors, vitamins, and other ingredients. The bacterium can be cultured in any size vessel, carboys or fermenters being well suited for large scale production. Temperature need not be controlled precisely, although growth is generally more rapid within the range from 5° C. to 38° C., and temperature control within this range is preferred. More preferred is culturing from 25° C. to 37° C., with culturing at about 25° C. being most preferred. The pH should be maintained in the pH range from 6.5 to 8.5 in order to maximize growth although growth may occur at other pH values.

Preferred growth mediums include Trypticase Soy Broth (TSB) and Deoxycholate Citrate Agar as described by Govan, *J. Med. Microbiol.*, 8: 513–522 (1975) supplemented with 3 mM $MgCl_2$. Supplementation of media with this or a similar level of a divalent cation promotes the production of high molecular weight alginate. A similar level of calcium or strontium may also be used. Chloride is the preferred counter-ion although others, such as nitrate, are possible.

It is also preferred to grow mucoid strains in humidified chambers, particularly for growth at higher temperatures.

The mucoid exopolysaccharide purification technique described herein may be employed with any bacteria which produces an exopolysaccharide, not just with the strain which produces the antigen of this invention. Other bacteria which may be used with this purification process include mucoid strains of *Escherichia coli*, *Azotobacter vinlandii*, and members of the genus *Flavobacterium*. The mucoid exopolysaccharides isolated from these bacteria, however, are not intended to be used in the other aspects of the present invention disclosed herein.

The bacteria may be harvested either continuously or in batches by centrifugation or filtration, with replacement of nutrient as needed. The collected cell paste may be used immediately, or it may be frozen and stored for up to several years, preferably at −20° C. or lower.

The bacterial antigen of the invention is isolated from the crude cell paste. Any procedure which isolates the mucoid exopolysaccharide from the bacteria is suitable for use in producing the antigen of the invention. Preferably, the first step of isolation involves washing the bacteria to remove the external polysaccharide coat without disrupting the cell contents. Suitable washing techniques are well known. Prefered washing techniques include washing with phosphate buffered saline (pH about 7.2) or with a solution of EDTA, preferably about 0.8 molar. In a preferred washing technique, one of these solutions is poured onto a culture plate containing the bacteria, and the growth is scraped off with a glass rod. The pooled suspensions are heated at from 50° C. to 70° C. for about 1 hour. The slurry is then mixed, and the bacteria are removed by centrifugation. Crude mucoid antigen may be obtained by dialyzing this crude extract and then removing water.

A key step of the preferred isolation technique of the present invention involves treating the dissolved mucoid exopolysaccharide with a divalent cation, preferably $Ca^{2+}$, at some point during the isolation technique in order to form a precipitate. This precipitate is then separated from the supernatant, and the precipitate is redissolved in EDTA, a salt of EDTA (preferably a sodium salt), or a similar chelating agent capable of chelating calcium and other divalent ions, such as EGTA, dimethylglyoxime, 1,10-phenanthroline, and alpha-benzoin oxime. If preferred, magnesium or another divalent ion may be used instead of calcium in the precipitation step. Other ions which may be used include $Fe^{2+}$, $Pb^{2+}$, $Sr^{2+}$, $Cu^{2+}$, $Zn^{2+}$, $Ni^{2+}$, $Co^{2+}$, $Mn^{2+}$, and $Sn^{2+}$. Addition of the divalent ion to the concentration greater than 0.2 molar is preferred. The use of a divalent cation to precipitate the mucoid exopolysaccharides followed by removal of the divalent ion with a chelating agent, thereby causing the mucoid exopolysaccharides to go back into solution, provides an easy method of separating the mucoid exopolysaccharides from other polysaccharides and from nucleic acids produced by the bacteria.

The most preferred initial step of the isolation procedure is extraction of the mucoid exopolysaccharide into phosphate buffered saline as described above, followed by precipitation with calcium chloride at a concentration of 0.2 molar and redissolving the precipitate in 0.8M EDTA, pH 9.0.

Additional steps may be used to further purify the mucoid antigens. A preferred purification step is ion exchange chromatography on a support having pendant amino groups. Preferred pendant groups are diethylaminoethyl groups. DEAE-Sephadex (Pharmacia Fine Chemicals, Uppsala, Sweden) is a preferred chromatography material. The antigen is applied as a dilute solution to the ion exchange column, preferably about 500 mg antigen per 200–225 $cm^3$ of the ion exchange material. A preferred medium for dissolving the crude mucoid antigens and equilibrating the column is 0.05M Tris-0.025M EDTA buffer, pH 8.2. The antigen concentration in the solution applied to the column is preferably about 2–10 mg/ml, preferably about 5 mg/ml. After the antigen is applied to the column, the column is washed with several column bed volumes of the buffer in which the antigen is dissolved. About 5 column bed volumes is preferred. The eluant at this stage is discarded. Antigen adhering to the column is eluted by sequential washings with increasing concentration of a salt, preferably sodium chloride. A sodium chloride concentration of about 0.4M is sufficient to elute the desired antigens. The column eluate is monitored, for example, by refractive index, to identify fractions containing eluting antigens. These fractions are collected.

The collected antigen fractions from the ion exchange column column may be concentrated by either precipitating with calcium as previously described or by precipitating with an organic solvent, preferably ethanol. Other concentration techniques, such as ultrafiltration, may also be used. Precipitation with a 95% alcohol to a final concentration of 80% alcohol in order to precipitate antigen is preferred when an organic solvent is used for precipitation.

Another preferred purification step involves selection of high molecular weight antigens by any process capable of separating high molecular weight from low molecular weight material. The process should be capable of separating antigens having a molecular weight of more than 100,000 daltons from antigens of lower molecular weight. Molecular sieves are preferred for this purpose. A preferred molecular sieve material is Sephacel S-300. Any molecular seive material may be used which significantly retards the passage of a Dextran T-70 molecular weight marker. When a Sephacel S-300 column is used, the mucoid antigen of the present invention elutes just past the void volume and ahead of the Dextran T-70 molecular weight marker. Eluant from a molecular sieve column may be monitored by absorbance of ultraviolet light (preferably at 206 nm). The eluant fractions containing the mucoid antigen may be concentrated by any of the steps previously described, preferably by precipitation with calcium chloride to 0.25M and centrifugation, particularly if this is the last step of the purification technique. If the mucoid antigen is precipitated with calcium chloride, it is typically redissolved in EDTA and dialyzed prior to removal of water. At all stages throughout purification, lyophilization is preferred as a means of water removal.

The purification technique of the invention may involve these steps in any order. A calcium precipitation-/EDTA dissolution step is preferred as the last step of the process even if it is also used at an earlier stage. A preferred procedure involves initial isolation of a crude antigen fraction by extracting the bacterial paste with either an EDTA solution or a phosphate buffered saline solution. If a phosphate buffered saline solution is used, calcium chloride is added to the resulting solution to precipitate the mucoid antigen, which is then redissolved in EDTA. The resulting material is then applied in a buffered solution to an ion exchange column as previously described. The eluant of the ion exchange column is collected as described and applied to a molecular sieve material in order to recover high molecular weight antigens. A calcium precipitation/ETDA dissolution step is then used to purify the eluant from the molecular sieve column.

As is well understood by those skilled in the art of polysaccharide purification, additional steps may be included to further purify the mucoid exopolysaccharide. These steps may include but are not limited to digestion with enzymes that destroy nucleic acids and proteins. Furthermore, equivalent buffering agents and solutions of similar osmolality and ionic strength (for example, to replace the buffered salt solution that is used in the ion exchange chromatography step) may be used throughout this process.

A particularly preferred method for isolating the antigen of the invention or for isolating other antigens from different strains of *Pseudomonas aeruginosa* or from strains of other bacteria which produce mucoid exopolysaccharides includes the following sequence of steps. A mucoid exopolysaccharide-producing bacteria is grown to conflence on plates. For example, *P. aeruginosa* may be grown on TSB supplemented with 3 mM $MgCl_2$ at 37° C. in a humidified atmosphere for 48 hr. About 10 ml of 0.8M EDTA, pH 9.0, is poured onto the plate and the growth is scraped off. The pooled suspensions from several plates are heated at about 60° C. for about 1 hour. The slurry is then mixed (for example, in a blender) for about 60 seconds. The bacteria are then removed by centrifugation. The crude mucoid antigen is dialyzed against running tap water and then against deionized water prior to being lyophilized.

Purified mucoid antigen is then obtained from the crude preparation. The crude mucoid antigen is dissolved in 0.05M tris–0.025M EDTA buffer, pH 8.2 (5 mg/ml final concentration) and applied to a 2.6×40 cm column of DEAE-Sephadex equilibrated in the same buffer. About 500 mg of crude antigen is applied per ion exchange column. The column is then washed with about 5 column void volumes of the buffer, and then unbound material is discarded. The ion-exchange column is then eluted by sequential washings with increasing concentrations of sodium chloride in the same buffer solution, first increasing the sodium chloride concentration to 0.2M and then to 0.4M. Fractions containing antigen are identified by a refractive index monitor or other method capable of identifying the presence of polysaccharides. Fractions containing antigen are pooled and precipitated with 95% alcohol to a final concentration of 80%. The collected precipitate is redissolved in 0.05M TRIS, pH 7.3. The redissolved precipitate is then digested with the enzymes DNAase and RNase as described in *Pier et al, Infect. Immun.*, 22, 908–918 (1978), which is herein incorporated by reference. A dilute amount (0.001M) of a divalent cation is added to facilitate the activity of the nucleases. This concentration will not precipitate mucoid antigens. The nuclease-digested solutions are then applied to a 2.6×100 cm column of Sephacel S-300 equilibrated in phosphate buffered saline solution (0.1M phosphate, 0.15M NaCl, pH 7.2). The column eluate is monitored for adsorbance of ultraviolet light at 206 nm, and optically active fractions, eluting just past the void volume and prior to the known elution fraction of a Dextran T-70 molecular weight marker, are collected. The mucoid antigen is recovered by precipitation with $CaCl_2$ to 0.25M and centrifugation, redissolved in 0.8M EDTA, dialyzed for 48 hr against running tap water and then against several changes of deionized water, and lyophilized.

This preferred procedure of the invention produces a mucoid exopolysaccharide of greater than 99% purity. This level of purity is considerably greater than that which is normally obtained in the purification of polysaccharides. However, purity to this degree is not essential for carrying out all the objects of the present invention. Accordingly, the present invention also encompasses mucoid exopolysaccharide from *Pseudomonas aeruginosa* 2192 isolated by any combination of these or other purification steps. For example, both crude antigen and antigen of 80% purity are considered part of this invention.

Mucoid exopolysaccharide from *Pseudomonas aeruginosa* 2192 is preferably stored in lyophilized form under vacuum. Any standard method of lyophilization may be used. The principal requirement for stable storage is dryness. Accordingly, lyophilized samples may also be stored under inert gases if they are maintained free from moisture.

Lyophilized antigens of the invention are easily reconstituted by the addition of water or other aqueous solutions. When used as an inducer of immune activity, reconstitution in physiological saline is preferred. Reconstituted samples are preferably used for inducing immune response less than 72 hr after reconstitution.

When the antigen of this invention is used to induce immune response in a human or animal, it is administered to a human or animal in an amount sufficient to induce an immune response. A minimum preferred amount is the amount required to elicit antibody formation to a concentration at least 4 times that which existed prior to administration. Antibody concentration is easily measured as is well known to those skilled in the art. For example, a hemagglutination assay of antibody titer may be used to measure antibody production. Such an assay is described in detail in the experimental section of this application. Typically, an initial dose suitable for administration would be 10–500 micrograms per dose, particularly when administration is to a human, the preferred target organism. This amount may be adjusted by a clinician doing the administration, as commonly occurs in the administration of vaccines and other agents which induce immune responses. Although a single administration has been shown to induce an immune response, multiple administrations may be carried out if desired or if required.

Administration by subcutaneous injection is preferred although other methods of administration which cause an immune response in the human or animal to which administration is being made may be carried out. For example, intramuscular, intradermal, and intranasal administration are also possible, as well as administration by bronchial levage. No adjuvants are required, although they may be used if desired. Administration of the mucoid exopolysaccharide as a solution in physiological saline is preferred. Other physiologic salt solutions may be substituted.

The most preferred use of the antigen of the invention is to induce an immune response in a human patient suffering from cystic fibrosis. Non-humnan use is preferably with laboratory aminals, such as mice, rabbits, dogs, cats, and monkeys. Induction of an immune response prior to colonization of the patient with *Pseudomonas aeruginosa* is preferred. Previous investigations have suggested that colonization of the respiratory track with *P. aeruginosa* induces antibodies incapable of opsonizing *P. aeruginosa* for phagocytic killing. However, Pennington et al, *J. Clin. Invest.*, 68, 1140–1148 (1981) demonstrated that guinea pigs preimmunized with *P. aeruginosa* lipopolysaccharide and then intratracheally challenged with mucoid *P. aeruginosa* in agar beads had a better clinical picture and fewer number of organisms in lung tissue 2 and 4 weeks post-challenge than did guinea pigs that were either not immunized or were immunized with lipopolysaccharide 2 weeks after infection. Thus, immunization prior to colonization with the organism immunized against is expected to be more effective than post-colonization immunizing.

The superiority of the present antigen from *P. aeruginosa* 2192 has been demonstrated by comparison of the immune response caused by this antigen and the immune response caused by two other strains of *P. aeruginosa*. Antisera were raised against both bacteria and purified mucoid antigens. Ouchterlony immunodiffusion and hemagglutination assays were performed in order to measure the ability of these bacteria and mucoid exopolysaccharide preparations to function as useful vaccines. The mucoid antigen from strain 2192 induced antibodies which reacted effectively with the antigens and bacteria of all three strains. Much lower cross-reactivity was seen with the sera induced by the antigens isolated from the other strains of *P. aeruginosa*. These experiments are described in detail in the experimental section.

The mucoid exopolysaccharide from strain 2192 has a different chemical makeup from the mucoid exopolysaccharides obtained from other strains. For example, the mucoid polysaccharide reported in Macone et al (supra) was one of the two comparison strains discussed above (strain 1). This strain produced a mucoid exopolysaccharide containing 45% glucuronic acid and 54% mannuronic acid. The mucoid exopolysaccharide from strain 2192 contained 52% glucuronic acid and 47.2% mannuronic acid. The second comparison strain was likewise different, having a ratio of mannuronic to glucuronic acid of about 3:1.

Thus, the mucoid polysaccharide from *P. aeruginosa* 2192 is chemically and immunologically distinct from the previously known mucoid exopolysaccharides isolated from *P. aeruginosa*. Of particular importance is the ability of this antigen to induce an immune response against multiple strains of *P. aeruginosa*. This unexpected property allows the production of a vaccine from a single organism rather than requiring a combination of different antigens isolated from different sources.

Having now generally described this invention, the same will be better understood by reference to certain specific examples, which are included herein for purposes of illustration only and are not intended to be limiting of the invention or any embodiment thereof, unless so specified.

EXAMPLE

Isolation and Immunochemical Characterization of the Mucoid Exopolysaccharide of *Pseudomonas Aeruginosa* 2191

MATERIALS AND METHODS

Bacterial strains employed. Strains of mucoid *P. aeruginosa* were obtained from the clinical bacteriology laboratory of the Children's Hospital Medical Center, Boston, Mass. Strains were determined to be mucoid by morphologic appearance and stored as stock cultures in Tripticase Soy Broth (TSB) at $-80°$ C. on glass beads. Nonmucoid revertant (NMR) strains were derived by serial passage of mucoid strains on Trypticase Soy Agar (TSA) plates until a nonmucoid bacterial colony (based on morphologic appearance) emerged. This colony was picked and streaked onto a second TSA plate. If complete nonmucoid growth was obtained, this plate was used as a source of stock cultures of NMR strains in TSB at $-80°$ C. In some instances, NMR strains were grown on TSA plates supplemented with 0.1M CaCl$_2$, which suppressed expression of the mucoid phenotype.

Culture of bacteria. Growth of bacterial strains was routinely done on TSA plates supplemented with 3 mM MgCl$_2$. Mucoid strains were also routinely grown in humidified chambers, which promoted the stable expression of the mucoid phenotype.

Antigens. Crude mucoid antigen was prepared from confluent plates of mucoid *P. aeruginosa* grown on TSA supplemented with 3 mM MgCl$_2$ at 37° C. in a humidified atmosphere for 48 hr. About 10 ml of 0.8M EDTA, pH 9.0, was poured onto the plate and the growth scraped off with a glass rod. The pooled suspensions were heated at 60° C. for 1 hour, the slurry was mixed in a Waring blender for 60 sec, and the bacteria were then removed by centrifugation. Th crude mucoid antigen was dialyzed extensively against running tap water and then against deionized water, prior to being lyophilized. The ability to maintain mucoid antigens in solution was dependent on the chelation of divalent cations by EDTA, since concentrations of divalent cations greater than 0.2M were found to precipitate the mucoid antigens out of solution.

Purified mucoid antigens were obtained from the crude preparations as follows: crude mucoid antigens were dissolved in 0.05M Tris–0.025M EDTA buffer, pH 8.2 (5 mg/ml final concentration) and applied to a 2.6×40 cm column of DEAE-Sephadex (Pharmacia Fine Chemicals, Uppsala, Sweden) equilibrated in the same buffer. Because of the viscosity of these solutions, about 500 mg of crude antigen was applied as a dilute solution to the ion-exchange column. This column was then washed with five column bed volumes of the Tris-EDTA buffer and the unbound material discarded.

Elution of the ion-exchange column was accomplished by sequential washes with increasing concentrations of NaCl. Thus the column was next washed with the Tris-EDTA buffer containing 0.2M NaCl and the eluate collected, alcohol precipitated (80% final concentration), redissolved in deionized water, dialyzed and lyophilized. The desired mucoid antigen was then eluted by washing with 0.4M NaCl in Tris-EDTA. The column eluate was monitored by a refractive index monitor (Waters Associates, Milford, Mass.) to identify fractions containing eluting antigen. These fractions were pooled and precipitated with 95% alcohol to a final concentration of 80%. The collected precipitate was redissolved in 0.05M Tris, pH 7.3, and digested with the enzymes DNAase and RNase as described in Pier et al, *Infect. Immun.*, 22, 908–918 (1978). A dilute amount (0.001M) of divalent cations were added to facilitate the activity of the nucleases. This concentration of divalent cations did not precipitate mucoid antigens. The nuclease-digested solutions were then applied to a 2.6×100 cm column of Sephacel S-300 equilibrated in phosphate buffered saline (PBS, 0.1M phosphate, 0.15M NaCl, pH 7.2). The column eluate was monitored for adsorbance of UV light at 206 nm (Uvicord S, LKB Instruments, Rockville, Md.), and optically active fractions, eluting just past the void volume and ahead of where a Dextran T-70 molecular weight market was known to elute, were collected. The mucoid antigen was recovered by precipitation with CaCl$_2$ to 0.25M and centrifugation, redissolved in 0.8M EDTA, and dialyzed for 48 hr against running tap water and then against several changes of deionized water. The resulting solution was lyophilized.

Material eluting in the 0.6M NaCl eluate from the ion-exchange column was recovered by ethanol precipitation, dialyzed, and lyophilized for biochemical and antigenic analyses.

Preparation of antisera. Antisera were raised to the mucoid organisms and the NMR strain 2192 via a series of IV injections of formalin-fixed bacterial cultures. Organisms grown for 24 hr on TSA plates with 3 mM MgCl$_2$ were suspended to an OD$_{650}$ of 1.0 in 1% formalin-PBS. After 24 hr at room temperature, the cells were washed three times in saline and resuspended to an OD$_{650}$ of 1.0. These suspensions were checked for sterility in TSB and thioglycollate media prior to their use. Individual rabbits (3 kg) were immunized for five days of the first week with 0.5 ml of a single formalin-fixed bacterial suspension, then with 1.0 ml for five days of the second and third weeks. Rabbits were bled from the ear 10 days after the final injection and the sera collected from clotted blood. Routine boosting and bleeding of the rabbits were carried out every one to two months.

Antisera to the purified mucoid antigens were raised in three kg rabbits, utilizing an initial subcutaneous injection of 0.5 mg antigen in complete Freund's adjuvant (CFA) given in the back of the neck. Five days later the swollen cervical lymph noted were directly injected with 0.5 mg antigen in CFA. One week later the animals were given 0.5 mg antigen in 0.5 ml saline IV every day for 1 week. The animals were bled seven days after the final injection, then boosted by IV injections and bled on a monthly basis.

Human sera used in these studies were obtained from the following sources: norman human sera (NHS) from adult laboratory personnel and medical students, NHS from pediatric patients (means age 14 years) undergoing either elective or orthopedic surgery at the Children's Hospital Medical Center, Boston, Mass., sera from CF patients (mean age not determined) either culture positive or culture negative for mucoid *P. aeruginosa* at the Ina Sue Perlmutter Cystic Fibrosis Center of the Children's Hospital Medical Center, Boston, Mass., collected by clinical investigators.

Serological analyses. Ouchterlony immunodiffusion was performed using 1% agarose in PBS. Immunoelectrophoresis (IEP) was performed as described in Pier et al, *Infect. Immun.*, 22, 908–918 (1978). Hammagglutination assays utilized thrice washed sheep red blood cells (SRBC) sensitized with crude mucoid antigens (see below). Sensitization was accomplished by mixing 1 ml of washed 10% SRBC with 10 mg of crude mucoid antigen at 37° C. for one hour with continuous tumbling. The SRBC were then washed five times with saline, resuspended in saline to a 1% final suspension, and 0.1% (final concentration) of glutaraldehyde added. After 24 hr of fixing, the cells were washed five times in saline and resuspended to 1% in saline. Sensitized cells generally remained usable for two months or more, but were routinely washed three times with saline prior to each daily use to remove inhibitory substances that were released from the cells during storage. The specificity of the sensitized SRBC for mucoid antigens was always assessed by testing the sensitized cells against sera adsorbed extensively with lyophilized bacteria of the homologous NMR strain. Hemagglutination inhibition assays were performed utilizing four HA units of diluted sera incubated with dilutions of the inhibitor being tested for 30 min prior to the addition of sensitized SRBC.

Adsorption of antisera. Antisera were adsorbed with either formalin-fixed and lyophilized mucoid or NMR bacteria (10 mg/ml serum) at 37° C. for two hr followed by incubation at 4° C. overnight with constant tumbling. The bacteria were then removed by centrifugation, and the sera were filtered through sterile 0.45 micrometer membranes and tested for HA activity. If residual HA titers were found in sera adsorbed with mucoid organisms, the sera were readsorbed until the titer was eliminated. Parallel sera adsorbed with an equivalent amount of NMR bacteria were always run to insure that these cells did not decrease the HA titers aginst sensitized SRBC.

Biochemical analyses. The protein content of the various preparations examined was determined by the method of Lowry et al, *J. Biol. Chem.*, 193, 265–275 (1951). Nucleic acids were determined by adsorbance of UV light at 254 nm utilizing a standard curve of RNA, not corrected for end adsorption effects of polysaccharides. Lipopolysaccharide was determined on the basis of the 2-keto-3-deoxyoctulosonic acid (KDO) content, as measured by the thiobarbituric acid assay described in Osborne et al, *Proc. Natl. Acad. Sci. U.S.A.*, 50, 449–506 (1963). Isoelectric focusing (IEF) of antigens in pH gradient gels was performed as described in Ma-Cone et al, *N. Eng. J. Med.*, 304, 1445–1449 (1981).

Determination of the carbohydrate constituents of the mucoid antigens was performed by GLC analyses. Material to be analyzed was both the purified mucoid antigen and this same material reduced twice with water soluble carbodiimide and sodium borohydride by the method of Taylor and Conrad, *Biochem.*, 11, 1383–1388 (1972). The use of EDTA in the extraction and purification steps of the preferred method of the invention markedly reduced the viscosity of the purified alginate, eliminating the need to perform a preliminary limited hydrolysis step previously described as necessary by others in order to reduce the exopolysaccharide with the carbodiimide reagent. Both intact and reduced exopolysaccharides were analyzed as the trimethyl silyl (TMS) derivitized esters following hydrolyses for 24 hr in 12% methanolic HCl, prepared with acetyl chloride and methanol (2 ml acetyl chloride/10 ml methanol). The TMS procedure was chosen since both gulose and mannose in the carbodiimide reduced alginate could be measured, as well as gluluronic and mannuronic acid in the intact alginate. This procedure also allowed for measurement of the amount of reduction by the carbodiimide reagent. GLC was performed on a Packard model 421 using a 4 mm by 6 ft column packed with 3% SE-30 on Gaschrom Q. Nitrogen carrier gas flowed at 33 cc/min. The temperature program was 140° for 3 min followed by a rise of 5° C. per min to 245° C., which was held for 5 min. Injector temperature was 200° C., and the flame ionization detector was at 250° C. Data recording and analyses were performed with a Hewlett Packard model 3388A integrator. Quantitation was performed by comparisons of the areas obtained from analyzed samples with those obtained for authentic standards, except for guluronic acid, which was determined from authentic alginic acid (Sigma Chemical Co., St. Louis, Mo.) after subtraction of the mannuronic acid level.

Statistics. The test for statistical significance in the distribution of the titers between the different population groups was a Mantel-Haenszel test, a statistics test for nonparametric distributions in two samples, as described in Miller, *Survival Analyses,* John Wiley and Sons, New York, 1981, page 94.

RESULTS

Purification of mucoid exopolysaccharide. Utilizing the procedure outlined in the methods section, crude and purified mucoid antigens from three strains (separate clinical isolates) of mucoid *P. aeruginosa* (nos. 1, 258, and 2192) were prepared. From the 0.4M NaCl eluate of the ion-exchange column, material that was both high in uronic acid content and serologically active was obtained (see below). This material was further purified by enzyme digestions, molecular sieve chromatography, and $CaCl_2$ precipitation. Yields of purified material were about 15% of the starting weight of crude antigen. The elution pattern of the alginate from the molecular sieve column indicated a molecular weight of >100,000. Inclusion of EDTA in the extraction and purification buffers greatly reduces the viscosity of alginate solutions. Addition of $CaCl_2$ up to a concentration of 0.1M greatly increased the viscosity of these solutions. Levels of $CaCl_2$ above 0.2M precipitated the alginic acid exopolysaccharide out of solution.

By Ouchterlony immunodiffusion analyses a single precipitin line was obtained with the purified mucoid antigen from each strain when tested against antisera prepared to whole mucoid organisms. These same precipitin lines were seen when antisera were extensively adsorbed with NMR organisms. Precipitin lines were also observed when these sera were tested against crude mucoid extracts and the 0.4M NaCl eluate of the ion-exchange column. No precipitin lines were observed when NMR organisms were extracted with Tris-EDTA. A single precipitin arc was also obtained with purified mucoid antigen by IEP analysis. Analyses by IEF of the purified mucoid antigens also showed a single band when the gels were stained by the peridic acid-Schiff reagent for polysaccharides. All three mucoid antigens had an isoelectric pH of 4.2–4.6.

Biochemical analyses of mucoid antigens. Biochemical analyses of crude mucoid antigens are presented in Table 1. Crude antigen was composed of about 15–28% protein, 13–23% nucleic acids, 12–20% LPS and 23–42% total carbohydrates. The amount of LPS was based on a KDO content of 3% for *P. aeruginosa* LPS. Following application of crude antigen to the ion-exchange column, most of the protein and KDO positive material eluted in the 0.2M wash, whereas the 0.4M wash was composed almost exclusively of carbohydrate material. The material eluting in the 0.6M wash was primarily nucleic acid, but also contained a significant amount of carbohydrate material. The material eluting in the 0.4M NaCl fractions was further purified by nuclease digestions, molecular sieve chromatography and $CaCl_2$ precipitation (as described in the materials and methods section) for use in immunizing animals and serologic studies.

TABLE 1

Biochemical Analyses of Crude and Partially Purified Mucoid Exopolysaccharides

| Component* | Crude antigen | | | 0.2 M eluate | | | 0.4 M eluate | | | 0.6 M eluate | | |
| --- | --- | --- | --- | --- | --- | --- | --- | --- | --- | --- | --- | --- |
| | 1 | 258 | 2192 | 1 | 258 | 2192 | 1 | 258 | 2192 | 1 | 258 | 2192 |
| protein | 28 | 25 | 15 | 13 | 22 | 18 | 2 | 3 | 4 | 8 | 3 | <.5 |
| nucleic acid | 20 | 23 | 13 | 2 | 3 | 2 | 3 | 2 | <.5 | 43 | 56 | 13 |
| LPS+ | 19 | 12 | 20 | 22 | 10 | 12 | <.5 | <.5 | <.5 | <.5 | <.5 | <.5 |
| carbohydrate | 23 | 32 | 42 | 9 | 12 | 8 | 79 | 93 | 89 | 22 | 16 | 33 |

*see materials and methods for procedures used
represents percent of total amount of material
+amount of LPS based on KDO content of about 3% for *P. aeruginosa* LPS The biochemical analyses of the purified mucoid antigens are presented in Table 2. All three preparations were >99% uronic acid by quantitative GLC. Both strain 1 and 2192 mucoid preparations had a ratio of mannuronic acid to guluronic acid of about 1:1. Strain 258 had a ratio of mannuronic to guluronic acid of about 3:1.

TABLE 2

Biochemical Analyses of Purified Mucoid Exopolysaccharides

| Component* | Purified mucoid exopolysaccharide from strain | | |
| --- | --- | --- | --- |
| | 1 | 258 | 2192 |
| protein | <.5 | <.5 | <.5 |
| nucleic acid | <.5 | <.5 | <.5 |
| LPS | <.5 | <.5 | <.5 |
| carbohydrate total | 99.5 | 99.9 | 99.2 |
| guluronic acid (%) | 45 | 23 | 52 |
| mannuronic acid (%) | 54.5 | 76.9 | 47.2 |

*see materials and methods for procedures.
percentage of total weight.

Serologic activity of antigens and antisera. When antisera raised to either whole mucoid organisms, strain 2192 NMR organisms, or purified mucoid antigens were tested for HA activity against SRBC sensitized with crude mucoid antigen, significant titer elevations over pre-immunization levels were observed (Table 3). The specificity of the antibody for the mucoid antigen component was tested by adsorbing these sera with formalin-fixed and lyophilized mucoid and NMR cells. In all cases adsorption with mucoid cells completely removed HA activity of the sera, while adsorption with an equivalent number of NMR cells only slightly reduced the HA titers. The fact that the antiserum raised to strain 2192 NMR cells also contained antibody with specificity for mucoid substance showed that the morphologic appearance criterion used to determine that this strain had ceased production of mucoid substance was insufficient. Antisera raised to a strain of 2192 NMR serially passaged on TSA plates with 0.1M CaCl₂, a process found to suppress alginate synthesis (also by a morphologic criterion), did not contain antibody to the mucoid material (Table 3).

TABLE 3

Hemagglutination Titers of Antisera

| Serum raised to: | | Sheep red blood cells sensitized with crude mucoid antigen from strain: | | |
| --- | --- | --- | --- | --- |
| | | 1 | 258 | 2192 |
| strain 1 | organisms | 1024* | 8 | ≧2048 |
| | mucoid antigen | 128 | 8 | 128 |
| strain 258 | organisms | 16 | 1024 | 256 |
| | mucoid antigen | 8 | 128 | 32 |
| strain 2191 | organisms | ≧2048 | 16 | ≧2048 |
| strain 2192 | mucoid antigen | 128 | 8 | 128 |
| strain 2192 | NMR organisms | 16 | 4 | 128 |
| strain 2192 | NMR organisms passed on 0.1 M CaCl₂ plates | 2 | 2 | 2 |

*represents titer (reciprocal of dilution) of serum showing positive agglutination of the sensitized cells. All pre-immunization sera had titers of 2 or less. Each indicated serum was obtained from a single rabbit.

The serologic cross-reactions among the three mucoid antigens and the antibodies directed to them (Table 3) were also examined. Antisera prepared against the three mucoid strains and the respective purified mucoid antigens all contained high titers of antibody directed at strain 2192 sensitized SRBC. Antibody raised to either strain 2192 organisms or purified mucoid antigen also agglutinated SRBC sensitized with the other two mucoid antigens, although the titers against strain 258 sensitized SRBC were low. Antisera raised to strain 1 and 258 organisms and purified mucoid antigens also show cross agglutination, but with significantly lower titers than that found against strain 2192.

To test the serologic relationships of these three antigens, an HAI assay was used. When purified antigens from these three strains were used as inhibitors in an HAI assay, it was found that each mucoid antigen could inhibit the reaction of antiserum raised to strain 2192 purified mucoid antigen and SRBC coated with strain 2192 crude antigen (Table 4). For the other two antigens, only the homologous mucoid antigen inhibited the reaction of sensitized SRBC with 4 HA units of the homologous antiserum (Table 4). All three mucoid antigens were able to inhibit the reactions of antisera raised to strains 1 and 258 with SRBC sensitized with strain 2192 mucoid antigen. Similarly, all three antigens inhibited the reaction of antiserum raised to strain 2192 antigen with SRBC sensitized with mucoid antigens from strains 1 and 258. These data were best interpreted as showing that strain 2192 contains a preponderant amount of a common serologic determinant. The other two mucoid antigens appear to have a type specific determinant in addition to this common one, since only they could inhibit the reaction of homologous antibody and antigen. Presumably this result is due to a higher titer of antibody to the type specific determinant in antisera raised to strains 1 and 258 purified mucoid antigens, allowing for agglutination of sensitized SRBC at the dilution of 4 HA units used in the HAI assay.

TABLE 4

Hemagglutination Inhibition Results

| Antigen-Antiserum system | | Inhibitor-purified mucoid antigen from strain | | |
|---|---|---|---|---|
| Crude antigen on SRBC from strain: | Antiserum raised to purified antigen from strain: | 1 | 285 | 2192 |
| 1 | 1 | 10* | — | — |
| 258 | 258 | — | 9 | — |
| 2192 | 2192 | 10 | 6 | 10 |
| 2192 | 1 | 10 | 9 | 10 |
| 2192 | 258 | 7 | 6 | 9 |
| 1 | 2192 | 7 | 6 | 8 |
| 258 | 2192 | 8 | 5 | 9 |

*represents reciprocal of $\log_2$ dilution (maximum 10) of 5 mg/ml solution of inhibitor giving positive inhibition.
—, no inhibition at highest concentration tested.

Documenting the specificity of the serologic reaction for mucoid antigens was important, and this was done utilizing the HAI assay. Since positive inhibition of the HA assay was obtained with low concentrations (dilution to $\log_2$ 10 of 5 mg/ml) of crude or purified mucoid antigens (Table 4 or 5), material was extracted from NMR cells as a control in an identical manner to the extraction procedure for mucoid P. aeruginosa strains. These extracts possessed only minimal inhibitory activity (Table 5). Serial two-fold dilutions of culture supernates from broth-grown mucoid and NMR organisms showed inhibitory activity only in the mucoid organism broth supernate. The inhibitory activity of purified mucoid antigen was destroyed by either periodate oxidation or carbodiimide plus borohydride reduction (Table 5). Periodate cleaves the bond between vicinal carbon atoms containing hydroxyl groups, commonly found in monosaccharides. Carboimimide plus sodium borohydride reduces the carboxylic acid moity of the uronic acid to the alcohol form found in hexoses. This confirmed that the reaction of antibody and mucoid antigens required an intact uronic acid structure. These results also showed that the sensitization of SRBC with crude mucoid antigen resulted in an HA assay with specificity for mucoid exopolysaccharide.

TABLE 5

Hemagglutination Inhibition Testing

| Inhibitor | Initial concentration (mg/ml) | Reciprocal of $\log_2$ dilution of initial concentration giving positive inhibition of the antigen-antibody* system from strain | | |
|---|---|---|---|---|
| | | 1 | 258 | 2192 |
| crude homologous mucoid antigen | 5 | 10 | 10 | 10 |
| crude homologous NMR cell extract | 5 | 1 | 2 | — |
| Pure mucoid antigen | 5 | 10 | 9 | 10 |
| periodate oxidized | 5 | — | — | — |
| carbodiimide reduced | 5 | — | 1 | 1 |

*antigen-antibody system tested was crude mucoid antigens sensitized onto SRBC and a 4 HA unit dilution of antisera raised to pure mocoid antigens.
—, no inhibition at highest concentration tested.

The serologic diversity of antigenic types of mucoid organisms found in clinical isolates of mucoid P. aeruginosa obtained from CF sputum cultures was next examined using the HAI assay. Crude antigen extracts from 40 strains of mucoid P. aeruginosa all showed inhibitory activity against rabbit antiserum raised to strain 2192 purified mucoid antigen and SRBC sensitized with crude 2192 antigen. Only 1 of the 40 strains could inhibit the strain 1 antigen-antiserum system, and none of the 40 strains inhibited the strain 258 antigen-antiserum system. This further confirmed that strain 2192 mucoid antigen possesses a serologic epitope shared among most mucoid P. aeruginosa exopolysaccharides.

By utilizing SRBC sensitized with strain 2192 crude mucoid antigen, the distribution of antibody titers to this mucoid exopolysaccharide in sera obtained from normal adults and children as well as from mucoid P. aeruginosa culture positive and negative CF patients was determined. The frequency distribution plot is shown in the FIGURE. There was a highly significant ($p<0.001$) difference in the titers found in the population of mucoid P. aeruginosa positive CF patients compared to the titers found in sera from normal adults, normal children, and culture negative CF patients. There was no significant ($p=0.3$–$0.45$) difference in the distribution of titer among these latter three groups compared to each other. Interestingly, a number of non-CF individuals with high titered antibody to the strain 2192 mucoid antigen were found. When these sera were adsorbed with mucoid or NMR bacteria from the 2192 strain, HA activity remained only in the sera adsorbed with NMR organisms, confirming the specificity of the antibody for mucoid antigens. The fact that all CF culture positive patients had a titer of at least 32 versus SRBC sensitized with 2192 crude antigen further indicated that this antigen contains a broadly reactive determinant common to mucoid P. aeruginosa exopolysaccharides. 68.5% of mucoid P. aeruginosa cuture positive CF patients had titers of $\geq 512$, compared to 9–12% of persons in the other groups with titers this high.

The invention now being fully described, it will be apparent of one of ordinary skill in the art that many changes and modifications can be made thereto without departing from the spirit or scope of the invention as set forth herein.

What is claimed as new and desired to be secured by Letters Patent of the United States:

1. A bacterial antigen comprising isolated mucoid exopolysaccharide comprising a polymer uronic acid formed principally from mannuronic and guluronic acids having the antigenic characteristics of Pseudomonas aeruginosa 2192.

2. The antigen of claim 1 in purified form containing no more than 20% non-mucoid exopolysaccharide material of biological origin.

3. The antigen of claim 2 containing no more than 1% non-mucoid exopolysaccharide material of biological origin.

UNITED STATES PATENT AND TRADEMARK OFFICE
CERTIFICATE OF CORRECTION

PATENT NO. : 4,578,458
DATED : March 25, 1986
INVENTOR(S) : Gerald B. PIER

It is certified that error appears in the above-identified patent and that said Letters Patent is hereby corrected as shown below:

-- Column 2, lines 2, 4, 10 and 12, delete "polysaccharide" and insert therefor --exopolysaccharide--.

line 36, delete "spatum" and insert therefor -- sputum --.

Column 5, line 14 delete "column", first occurance.

Column 7, line 46, delete "levage" and insert therefor -- lavage --.

line 61, delete "Pennigton" and insert therefor -- Pennington --.

Column 10, line 46, delete "Hammagglutina-" and insert therefor -- Hemmagglutina- --.

Column 11, line 51, delete "gluluronic" and insert therefor -- guluronic --.

Column 12, line 31, delete "alginic acid" and insert therefor -- mucoid --.

line 46, delete "peridic" and insert therefor -- periodic --.

UNITED STATES PATENT AND TRADEMARK OFFICE
CERTIFICATE OF CORRECTION

PATENT NO. : 4,578,458
DATED : March 25, 1986
INVENTOR(S) : Gerald B. PIER

Page 2 of 2

It is certified that error appears in the above-identified patent and that said Letters Patent is hereby corrected as shown below:

Column 13, TABLE 3, last line delete "numeral 2191" and insert therefor -- 2192 --.

Column 14, TABLE 3-continued, first entry under "Serum raised to:", change "mucoid antigen" to -- strain 2192 mucoid antigen --.

Signed and Sealed this

Twentieth Day of January, 1987

Attest:

DONALD J. QUIGG

*Attesting Officer*  *Commissioner of Patents and Trademarks*